(12) United States Patent
Castaldi et al.

(10) Patent No.: US 6,703,505 B2
(45) Date of Patent: Mar. 9, 2004

(54) PROCESS FOR THE PREPARATION OF HIGH PURITY PEMIROLAST

(75) Inventors: Graziano Castaldi, Briona (IT); Erminio Oldani, Cornaredo (IT)

(73) Assignee: Dinamite Dipharma S.p.A., Basiliano (IT)

( * ) Notice: Subject to any disclaimer, the term of this patent is extended or adjusted under 35 U.S.C. 154(b) by 0 days.

(21) Appl. No.: 10/196,260

(22) Filed: Jul. 17, 2002

(65) Prior Publication Data

US 2003/0032805 A1 Feb. 13, 2003

(30) Foreign Application Priority Data

Aug. 10, 2001 (IT) ...................................... MI2001A1764

(51) Int. Cl.$^7$ ............................................. C07D 239/70
(52) U.S. Cl. ....................................................... 544/282
(58) Field of Search .......................................... 544/282

(56) References Cited

U.S. PATENT DOCUMENTS

| 4,122,274 A | 10/1978 | Juby | 544/282 |
| 5,254,688 A | * 10/1993 | Sano et al. | 544/282 |

FOREIGN PATENT DOCUMENTS

| DE | 243 821 A3 | 3/1987 |
| EP | 0 462 834 A1 | 10/1991 |
| WO | 93/25557 | 12/1993 |

* cited by examiner

Primary Examiner—Alan L. Rotman
Assistant Examiner—Tamthom N. Truong
(74) Attorney, Agent, or Firm—Young & Thompson

(57) ABSTRACT

A novel process for the purification of Pemirolast, whose potassium salt is an anti-allergic pharmaceutical product, is disclosed.

5 Claims, No Drawings

PROCESS FOR THE PREPARATION OF HIGH PURITY PEMIROLAST

FIELD OF THE INVENTION

The present invention relates to a novel process for the purification of Pemirolast, whose potassium salt is an anti-allergic pharmaceutical product.

BACKGROUND OF THE INVENTION

Pemirolast, or 9-methyl-3-(1H-tetrazol-5-yl)-4H-pyrido-[1,2-a]-pyrimidin-4-one, has the following formula:

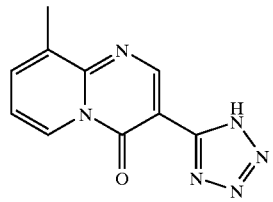

Several patents disclose processes for the preparation of Pemirolast Potassium.

According to all known methods, the product is firstly obtained in the acid form and then converted into the corresponding potassium salt.

As the product recovered in the acid form is very poorly soluble in conventional solvents, it always contains several by-products which can hardly be removed and only with remarkable losses in yields. The purification is usually carried out either directly on the acid form or on the corresponding potassium salt.

SUMMARY OF THE INVENTION

A novel process for the purification of Pemirolast acid form which provides high purity (>99,8% HPLC) and high yields (>85%) has now been found, and this is the object of the present invention.

The process of the invention comprises the salification of Pemirolast acid form in the presence of an amount of a primary or secondary amine ranging from 1 equivalent to 1.5 equivalents relative to Pemirolast and an amount of protic solvents such as water, $C_1$–$C_3$-alcohols or mixtures thereof ranging from 1 volume to 10 volumes relative to Pemirolast. The use of a 2:1 methanol:water mixture is preferred.

The salification is carried out at a temperature which allows to completely solubilize the salt, generally at a temperature ranging from 20 to 100° C., preferably from 40 to 80° C. When the solubilization is complete, the solution is acidified with mineral or organic acids to pH ranging from 2 to 4 in order to promote the precipitation of Pemirolast in the acid form which is then filtered, washed and dried to give a product with >99.8% HPLC purity. Suitable acids comprise formic acid, acetic acid and hydrochloric acid.

Said product can then be transformed into the corresponding potassium salt without further purification.

Primary amines for use according to the invention are $C_1$–$C_6$-alkylamines, or arylamines wherein the aryl residue can be phenyl, naphthyl or an optionally substituted aromatic heterocyclic nucleus.

Secondary amines for use according to the invention are di(C–$C_6$)alkylamines, alkylarylamines or diarylamines, wherein the alkyl or aryl residues are as defined above, or are an aliphatic and aromatic substituent and wherein the meanings for aliphatic and aromatic are those indicated above.

DETAILED DESCRIPTION OF THE INVENTION

The invention is illustrated in greater detail in the following examples.

EXAMPLE 1

A suspension of 9-methyl-3-(1 H-tetrazol-5-yl)-4H-pyrido-[1,2-a]-pyrimidin-4-one (68.5 g; 0.3 mols) in methanol (420 ml) and water (210 ml) heated at 50° C. is added with a 40% N-methylamine aqueous solution (30 ml, 0.35 mols) to pH=10. The solution is heated at 68–70° C., and acidified with formic acid (21 ml) to pH=3. After completion of the addition the mixture is kept at 68–70° C. for about 15 minutes and then cooled to 20–25° C. The precipitate is filtered, washed with methanol and dried under vacuum at 40° C. to give 9-methyl-3-(1 H-tetrazol-5-yl)-4H-pyrido-[1,2-a]-pyrimidin-4-one with >99.8% HPLC purity (63 g, 92% yield).

EXAMPLE 2

9-Methyl-3-(1 H-tetrazol-5-yl)-4H-pyrido-[1,2-a]-pyrimidin-4-one (63 g, 0.28 mols) is suspended in methanol (1000 ml). The resulting suspension is kept at 45° C. and slowly added with a 45% potassium hydroxide aqueous solution to pH 9–9.5. The suspension is stirred at 45° C. for about 15 minutes and then cooled to 20° C. The precipitate is filtered, washed with methanol and dried under vacuum at 80° C., to obtain Pemirolast Potassium (71.9 g; 0.27 mols, 96% yield) with HPLC purity >99.8%. $^1$H NMR($D_2O$, TMS) d (ppm): 2.02 (s, 3H); 6.83 (t, 1H); 7.22 (d, 1H); 8.18 (s, 1H); 8.47 (d, 1H).

What is claimed is:

1. A process for the purification of Pemirolast comprising:
   a) salifying crude Pemirolast with a primary or secondary amine in the presence of a 2:1 methanol/water mixture;
   b) acidifying the solution obtained in a) by addition of mineral or organic acids to a pH ranging from 2 to 4; and
   c) isolating precipitated Pemirolast, and optionally transforming the precipitated Pemirolast into the corresponding potassium salt.

2. The process as claimed in claim 1, wherein the primary amine is selected from C1–C6 aliphatic amines or arylamines.

3. The process as claimed in claim 1, wherein the secondary amine is selected from di(C1–C6)alkylamines, alkylarylamines or diarylamines.

4. The process as claimed in claim 1, wherein step b) is carried out with formic acid.

5. The process as claimed in claim 2, wherein step b) is carried out with formic acid.

* * * * *